US008350097B2

(12) United States Patent  
Jenkins (10) Patent No.: US 8,350,097 B2  
(45) Date of Patent: *Jan. 8, 2013

(54) THERAPEUTIC COMPOUNDS

(75) Inventor: Thomas E. Jenkins, Half Moon Bay, CA (US)

(73) Assignee: Signature Therapeutics, Inc., San Carlos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/437,802

(22) Filed: Apr. 2, 2012

(65) Prior Publication Data

US 2012/0196939 A1 Aug. 2, 2012

Related U.S. Application Data

(63) Continuation of application No. 12/596,711, filed as application No. PCT/US2008/063088 on May 8, 2008, now Pat. No. 8,173,849.

(60) Provisional application No. 60/928,345, filed on May 9, 2007, provisional application No. 60/928,416, filed on May 9, 2007.

(51) Int. Cl.
   *C07C 39/24* (2006.01)
   *C07C 39/06* (2006.01)
   *C07C 261/00* (2006.01)
   *A61K 31/05* (2006.01)

(52) U.S. Cl. ........ 568/775; 568/778; 568/780; 560/157; 514/736; 514/737

(58) Field of Classification Search .................. 568/775, 568/778, 780; 514/731, 737; 560/157
See application file for complete search history.

(56) References Cited

U.S. PATENT DOCUMENTS

| 2,747,982 | A | * | 5/1956 | Mussell | 504/174 |
| 4,056,635 | A | * | 11/1977 | Glen et al. | 514/731 |
| 4,452,817 | A | * | 6/1984 | Glen et al. | 514/730 |
| 4,798,846 | A | * | 1/1989 | Glen et al. | 514/731 |
| 5,714,520 | A | * | 2/1998 | Jones et al. | 514/731 |
| 5,731,355 | A | * | 3/1998 | Jones et al. | 514/731 |
| 5,908,869 | A | * | 6/1999 | Jones et al. | 514/731 |
| 6,140,374 | A | * | 10/2000 | May et al. | 514/731 |
| 7,731,356 | B1 | * | 6/2010 | Gilbert | 351/157 |

FOREIGN PATENT DOCUMENTS

WO   2006033911   3/2006

OTHER PUBLICATIONS

Adams et al. "Propofol-Induced Injection Pain: Comparison of a Modified Propofol Emulsion to Standard Propofol with Premixed Lidocaine" Anesthesia and Analgesia, vol. 99, (2004), p. 1076-1079.
Baker et al. "Propofol: the challenges of formulation" Anesthesiology, vol. 103, (2005), p. 860-876.
Bocian et al, "Propofol (Diprivan)1_A New Intravenous Anesthetic with Applications for Outpatient Ambulatory Surgery" the journal of foot surgery, vol. 31 (1992) p. 603-606.
Bruce et al. "Oxidative Coupling of Some 2,6-Disubstituted Phenols" Polymer, vol. 10(8), (1969), p. 701-705.
Bryson Harriet M. et al. "Propofol: An Update of its Use in Anaesthesia and Conscious Sedation" Drugs, vol. 60, (1995) p. 613-669.
Doenicke, A.W. et al. "Reducing Pain During Propofol Injection: The Role of the Solvent" Anesth Analg, vol. 82, (1996), p. 472-474.
Doenicke et al. "Pharmacokinetics and Pharmacodynamics of Propofol in a New Solvent"Anesth Analg, vol. 85, (1997), p. 1399-1403.
Dubey, P.K. et al. "Pain on Injection of Lipid-Free Propofol and Propofol Emulsion Containing Medium-Chain Triglyceride: A Comparative Study" Anesthesia and Analgesia, vol. 101, (2005), p. 1060-2, table of contents.
Fulton Bret et al. "Propofol: A Pharmacoeconomic Appraisal of its Use in Day Case Surgery" PharmacoEconomics, vol. 9, (1996), p. 168-178.
Fulton Bret et al. "Propofol: An Overview of its Pharmacology and a Review of its Clinical Efficacy in Intensive Care Sedation" Drugs, vol. 50, (1995), p. 636-667.
Gabel, Ronald A. "Sedation/Analgesia—An Anesthesiologist's Perspective" (2002).
Glen, J.B. et al. "Pharmacology of an Emulsion Formulation of ICI 35 868" British Journal of Anaesthesia, vol. 56, (1984), p. 617-626.
Kam, E. et al. "Comparison of Propofol-Lipuro with Propofol Mixed with Lidocaine 10 mg on Propofol Injection Pain" Anaesthesia, vol. 59, (2004), p. 1167-1169.
Kanto J. et al. "Pharmacokinetic Implications for the Clinical Use of Propofol" Clinical Pharmacokinetics, vol. 17, (1989), p. 308-326.
Klement, W. et al "Pain on Injection of Propofol: Effects of Concentration and Diluent" Br J Anaesth, vol. 67, (1991), p. 281-284.
Larijani Ghassem E. et al. "Clinical Pharmacology of Propofol: An Intravenous Anesthetic Agent" DICP The Annals of Pharmacotherapy, vol. 23, (1989), p. 743-749.
Maleck W. H. "Propofol Induced Injection Pain: Comparison of a Modified Propofol Emulsion and Standard Propofol with Premixed Lidocaine" Anesth Analg, vol. 70, (2005), p. 100:1858.
Marinella M.A. "Propofol for Sedation in the Intensive Care Unit: Essentials for the Clinician" Repiratory Medicine, vol. 91, (1997), p. 505-510.
Miller "Effects on the Central Nervous System" Millers Anesthesia, (2005), p. 320-370.
Nathanson, M.H. et al. "Prevention of Pain on Injection of Propofol: A Comparison of Lidocaine with Alfentanil" Anesthesia and Analgesia, vol. 82, (1996), p. 469-471.
Nolan J. et al. "Pharmacokinetic of Propofol Administered by Infusion in Dogs Undergoing Surgery" British Journal of Anaesthesia, vol. 70, (1993), p. 546-551.
Nyman, Y. et al. "Propofol Injection Pain in Children: A Prospective Randomized Double Blind Trial of a New Propofol Formulation Versus Propofol with Added Lidocaine" British Journal of Anaesthesia, vol. 95, (2005), p. 222-225.
Ohmizo, H. et al. "Mechanism of Injection Pain with Long and Long-Medium Chain Triglyceride Emulsive Propofol" Canadian Journal of Anaesthesia [Journal Canadien d'Anesthesie], vol. 52, (2005), p. 595-599.

(Continued)

*Primary Examiner* — Sikarl Witherspoon
(74) *Attorney, Agent, or Firm* — Carol L. Francis; Khin K. Chin; Bozicevic, Field & Francis LLP (57) ABSTRACT

A (−)-stereoisomer of formula (I): (formula I), wherein X is H or F; or a pharmaceutically acceptable salt or pro drug thereof, is useful as an anesthetic.

41 Claims, 2 Drawing Sheets

OTHER PUBLICATIONS

Parmar, A.K. et al. "Pain on Injection of Propofol. A Comparison of Cold Propofol with Propofol Premixed with Lignocaine" Anaesthesia, vol. 53, (1998), p. 79-83.
Paul, M. et al. "Pharmacological Characteristics and Side Effects of a New Galenic Formulation of Propofol without Soyabean Oil" Anaesthesia, vol. 58, (2003), p. 1056-1062.
Picard, P. et al. "Prevention of Pain on Injection with Propofol: a Quantitative Systematic Review" Anesthesia and Analgesia, vol. 90, (2000), p. 963-969.
Rau, J. et al. "Propofol in an Emulsion of Long- and Medium-Chain Triglycerides: the Effect on Pain" Anesth Analg, vol. 93, (2001), p. 382-4 3rd contents p. 38.
Reich, D.L. et al. "Predictors of Hypotension after Induction of General Anesthesia" Anesthesia and Analgesia, vol. 101, (2005), p. 622-628.
Schaub, E. et al. "Pain on Injection: A Double-Blind Comparison of Propofol with Lidocaine Pretreatment Versus Propofol Formulated with Long- and Medium-Chain Triglycerides" Anesthesia and Analgesia, vol. 99, (2004), p. 1699-702, table of contents.
Shafer Steven L. "Advances in Propofol Pharmacokinetics and Pharmacodynamics" Journal of clinical anesthesia, vol. 5, (1993), p. 14-21.
Soltesz, S. et al. "Effect of a 0.5% Dilution of Propofol on Pain on Injection during Induction of Anesthesia in Children" Anesthesiology, vol. 106 (2007) p. 80-84.
Sun, et al. "A Comparison of Pain on Intravenous Injection between Two Preparations of Propofo" Anesthesia and analgesia, vol. 101, (2005), p. 675-8, table of contents.
Suzuki, H. et al. "Propofol Formulated with Long-/Medium-Chain Triglycerides Reduces the Pain of Injection by Target Controlled Infusion" Acta anaesthesiologica Scandinavica, vol. 50, (2006), p. 568-571.
Tan, C.H. et al. "The Effect of Ketamine Pretreatment on Propofol Injection Pain in 100 Women" Anaesthesia, vol. 53 (1998) p. 302-305.
Ueki, R. et al."Emulsion of Flurbiprofen Axetil Reduces Propofol Injection Pain Due to a Decrease in Free Propofol Concentration" Journal of Anesthesia, vol. 21, (2007), p. 325-329.
White Paul F. "Propofol: Pharmacokinetics and Pharmacodynamics" Seminars in Anesthesia, vol. 7, (Apr. 20, 1988).
Wong, W.H. et al. "Role of Tramadol in Reducing Pain on Propofol Injection", Singapore Medical Journal, vol. 42, (2001), p. 193-195.
Wouters, P.F. et al. "Hemodynamic Changes during Induction of Anesthesia with Eltanolone and Propofol in Dogs" Anesthesia and Analgesia, vol. 81, (1995), p. 125-131.
Yamakage, M. et al. "Changes in Concentrations of Free Propofol by Modification of the Solution" Anesthesia and Analgesia,vol. 101, (2005), p. 385-8, table of contents.
Zeller, A. et al. "Distinct Molecular Targets for the Central Respiratory and Cardiac Actions of the General Anesthetics Etomidate and Propofol" The FASEB journal, vol. 19, (2005), p. 1677-1679.
James, et al. Synthesis, Biological Evaluation, and Preliminary Structure-Activity Considerations of a Series of Alkylphenols as Intravenous Anesthetic Agents. J. Med. Chem. 1980, 23, 1350-1357.
Krasowski, et al. General Anesthetic Potencies of a Series of Propofol Analogs Correlate with Potency for Potentiation of gamma-Aminobutyric Acid (GABA) Current at the GABA-A receptor but Not with Lipid Solubility. Journal of Pharmacology and Experimental Therapeutics, American Society for Pharmacology and Experimental Therapeutics, US, vol. 297, No. 1, (2001), pp. 338-351.
Maciagiewicz, et al. Design and synthesis of propofol analogs as new anesthetic agents. Abstracts of Papers, 233rd ACS National Meeting, Chicago, IL, United States, Mar. 25-29, 2007 (2002).
Altomare et al., "Highly Water-Soluble Derivatives of the Anesthetic Agent Propofol: In Vitro and In Vivo Evaluation of Cyclic Amino Acid Esters" Eur J Pharm Sci., vol. 20, (2003), p. 17-26.
Concas et al. "The General Anesthetic Propofol Enhances the Function of Gamma-Aminobutyric Acid-Coupled Chloride Channel in the Rat Cerebral Cortex" Journal of neurochemistry, vol. 55 (1990), p. 2135-2138.
Concas et al., "Neurochemical Action of the General Anaesthetic Propofol on the Chloride Ion Channel Coupled with GABAA Receptors" BRES, vol. 16356, (1990), p. 225-232.
Fechner et al. "Comparative Pharmacokinetics and Pharmacodynamics of the New Propofol Prodrug GPI 15715 and Propofol Emulsion" Anesthesiology, vol. 101, (2004), p. 626-639.
Fechner et al. "Pharmacokinetics and Clinical Pharmacodynamics of the New Propofol Prodrug GPI 15715 in Volunteers" Anesthesiology, vol. 99 (2003), p. 303-313.
Fechner et al. "Sedation with GPI 15715, a Water-Soluble Prodrug of Propofol, Using Target-Controlled Infusion in Volunteers" Anesthesia and Analgesia, vol. 100, (2005), p. 701-706.
Jian Qiu et al. "2,6-Difluorophenol as a Bioisostere of a Carboxylic Acid: Bioisosteric Analogues of y-Aminobutyric Acid" J. Med. Chem., vol. 42, (1999), p. 329-332.
Sagara et al. "Propofol Hemisuccinate Protects Neuronal Cells From Oxidative Injury" J Neurochem., vol. 73(6), (1999), p. 2524-2530.
Sanna E et al. "Novel Properties of Homomeric,81-y-Aminobutyric Acid Type A Receptors: Actions of the Anesthetics Propofol and Pentobarbital" Molecular Pharmacology, vol. 47, (1995), p. 213-217.
Sneyd, J.R. "Recent Advances in Intravenous Anaesthesia" Br J Anaesth, vol. 93, (2004), p. 725-736.
Struys et al. "Aquavan Injection, a Water-Soluble Prodrug of Propofol, as a Bolus Injection: a Phase I dose-Escalation Comparison with Diprivan (part 2): Pharmacodynamics and Safety" Anesthesiology, vol. 103, (2005), p. 730-743.
Tan, et al. "Pain on Injection of Propofol" Anaesthesia, vol. 53, (1998) p. 468-476.
Thompson Sally-Anne et al. "Mechanism of Action of General Anaesthetics New Information from Molecular Pharmacology" Current Opinion in Pharmaologym, vol. 1 (2001), p. 78-83.
Tomlin, S.L..et al. "Stereoselective Effects of Etomidate Optical Isomers on Gamma Aminobutyric Acid Type A Receptors and Animals" Anesthesiology, vol. 88, (1998), p. 708-717.
Trapani, G.et al. "Propofol in Anesthesia. Mechanism of Action, Structure-Activity Relationships, and Drug Delivery" Current Medicinal Chemistry, vol. 7, (2000) p. 249-271.
Trapani, G. et al. "Propofol Analogues. Synthesis, Relationships between Structure and Affinity at GABAA Receptor in Rat Brain, and Differential Electrophysiological Profile at Recombinant Human GABAA Receptors" J Med Chem, vol. 41, (1998), p. 1846-1854.

* cited by examiner

THERAPEUTIC COMPOUNDS

The present application is a Continuation of application Ser. No. 12/596,711, filed May 18, 2010, which is a 371 National Phase Application of PCT/ US2008/063088 filed on May 8, 2008 which claims the benefit of U.S. provisional patent application No. 60/928,345 filed on May 9, 2007 and U.S. provisional patent application No. 60/928,416 filed on May 9, 2007.

BACKGROUND OF THE INVENTION

Propofol (2,6-diisopropylphenol) is an intravenous sedative/hypnotic agent used extensively for induction and maintenance of general anesthesia, sedation of critically ill patients and procedural sedation (e.g., endoscopy). See Langly, M. S, and Heel, R. C. *Drugs,* 1988, 35, 334-372. Propofol is only sparingly soluble in water and is currently marketed in a 10% soybean oil based lipid emulsion similar to formulations used for parenteral nutrition.

Propofol is a $GABA_A$ agonist that activates multiple $GABA_A$ receptor subtypes, which are ion channels that transport chlorine anions across cell membranes, in the central nervous system. Although propofol is achiral, racemic mixtures of a number of dialkyl phenols are known agonists of the $GABA_A$ receptor (James et al., *J. Med. Chem.* 23, 1350, 1980; Krasowski et al., *J. Pharmacol. & Exp. Therapeutics* 297, 338, 2001). James et al., report finding propofol to be superior in its overall profile to other analogues evaluated.

Propofol is preferred by many clinicians due to its excellent pharmacokinetic, pharmacodynamic, emergence and recovery profiles. However, undesired side-effects (e.g., respiratory depression, ICU syndrome, injection pain and hemodynamic effects) produced at or near the therapeutic dose greatly limit its utility in multiple clinical settings. Of particular concern are the hemodynamic effects. Administration of propofol, particularly in bolus form, often produces decreases in blood pressure without a compensatory increase in heart rate. A variety of clinical conditions are incompatible with the use of propofol because of undesired and potentially harmful hemodynamic consequences. Examples of such conditions include cardiovascular disease such as coronary artery disease, cardiomyopathy, ischemic heart disease, valvular heart disease, and congenital heart disease. Chronic hypertension, cerebrovascular disease, brain injury, and advanced age can make the use of propofol difficult or problematic because of its hemodynamic properties. Patients with acute blood loss, dehydration, or severe infection including those with hemorrhagic shock, hypovolemic shock, or septic shock may be exposed to excessive hazard were propofol employed. The hemodynamic properties of propofol may limit its use in patients receiving other medications or treatments such as spinal anesthesia, epidural anesthesia, or vasoactive medications.

SUMMARY OF THE INVENTION

The invention provides therapeutic compounds that demonstrate similar or improved pharmacological activity compared to propofol along with an improved hemodynamic profile. Accordingly, in one embodiment the invention provides a (−)-stereoisomer of formula (I):

wherein X is H or F, or a salt or prodrug thereof.

The invention also provides a pharmaceutical composition comprising a (−)-stereoisomer of formula (I) or a pharmaceutically acceptable salt or prodrug thereof and a pharmaceutically acceptable carrier.

The invention also provides a method to treat nausea, vomiting, migraine, neurodegenerative conditions of the nervous system (e.g., Friedrich's disease, Parkinson's disease, Alzheimer's disease, Huntington's disease, amyotrophic lateral sclerosis (ALS), multiple sclerosis (MS), Pick disease, etc.), trauma to the central nervous system (e.g., skull fracture and its resulting edema, concussion, contusion, brain hemorrhages, shearing lesions, subdural and epidural hematoma, and spinal cord injury (e.g., mechanical injury due to compression or flexion of the spinal cord)), seizures (e.g., epileptic seizures) or a free radical associated disease (e.g., ischemic reperfusion injury, inflammatory diseases, systemic lupus erythematosis, myocardial infarction, stroke, traumatic hemorrhage, cataract formation, uveitis, emphysema, gastric ulcers, neoplasia, radiation sickness, etc.) in an animal comprising administering an effective amount of a (−)-stereoisomer of formula (I) or a pharmaceutically acceptable salt or prodrug thereof to the animal.

The invention also provides a method for inducing or maintaining general anesthesia in an animal comprising administering an effective amount of a (−)-stereoisomer of formula (I) or a pharmaceutically acceptable salt or prodrug thereof to the animal.

The invention also provides a method for promoting sedation in an animal comprising administering an effective amount of a (−)-stereoisomer of formula (I) or a pharmaceutically acceptable salt or prodrug thereof to the animal.

The invention also provides a method for treating a migraine in an animal comprising administering an effective amount of a (−)-stereoisomer of formula (I) or a pharmaceutically acceptable salt or prodrug thereof to the animal.

The invention also provides a method for treating insomnia in an animal comprising administering an effective amount of a (−)-stereoisomer of formula (I) or a pharmaceutically acceptable salt or prodrug thereof to the animal.

The invention also provides a method for promoting an anxiolytic effect in an animal comprising administering an effective amount of a (−)-stereoisomer of formula (I) or a pharmaceutically acceptable salt or prodrug thereof to the animal.

The invention also provides a method for treating addiction withdrawal in an animal comprising administering an effective amount of a (−)-stereoisomer of formula (I) or a pharmaceutically acceptable salt or prodrug thereof to the animal.

The invention also provides a method for promoting an antiemetic effect in an animal comprising administering an effective amount of a (−)-stereoisomer of formula (I) or a pharmaceutically acceptable salt or prodrug thereof to the animal.

The invention also provides a method for agonizing a GABA receptor comprising contacting the receptor (in vitro or in vivo) with an effective amount of a (−)-stereoisomer of formula (I) or a pharmaceutically acceptable salt thereof.

The invention also provides a method for agonizing a GABA receptor in an animal comprising administering an effective amount of a (−)-stereoisomer of formula (I) or a pharmaceutically acceptable salt or prodrug thereof to the animal.

The invention also provides a (−)-stereoisomer of formula (I) or a pharmaceutically acceptable salt or prodrug thereof for use in medical therapy.

The invention also provides the use of a (−)-stereoisomer of formula (I) or a pharmaceutically acceptable salt or prodrug thereof to prepare a medicament for treating nausea, vomiting, migraine, neurodegenerative conditions of the nervous system (e.g., Friedrich's disease, Parkinson's disease, Alzheimer's disease, Huntington's disease, amyotrophic lateral sclerosis (ALS), multiple sclerosis (MS), Pick disease, etc.), trauma to the central nervous system (e.g., skull fracture and its resulting edema, concussion, contusion, brain hemorrhages, shearing lesions, subdural and epidural hematoma, and spinal cord injury (e.g., mechanical injury due to compression or flexion of the spinal cord)), seizures (e.g., epileptic seizures) or a free radical associated disease (e.g., ischemic reperfusion injury, inflammatory diseases, systemic lupus erythematosis, myocardial infarction, stroke, traumatic hemorrhage, cataract formation, uveitis, emphysema, gastric ulcers, neoplasia, radiation sickness, etc.) in an animal.

The invention also provides the use of a (−)-stereoisomer of formula (I) or a pharmaceutically acceptable salt or prodrug thereof to prepare a medicament for inducing or maintaining general anesthesia in an animal.

The invention also provides the use of a (−)-stereoisomer of formula (I) or a pharmaceutically acceptable salt or prodrug thereof to prepare a medicament for promoting sedation in an animal.

The invention also provides the use of a (−)-stereoisomer of formula (I) or a pharmaceutically acceptable salt or prodrug thereof to prepare a medicament for treating a migraine in an animal.

The invention also provides the use of a (−)-stereoisomer of formula (I) or a pharmaceutically acceptable salt or prodrug thereof to prepare a medicament for treating insomnia in an animal.

The invention also provides the use of a (−)-stereoisomer of formula (I) or a pharmaceutically acceptable salt or prodrug thereof to prepare a medicament for promoting an anxiolytic effect in an animal.

The invention also provides the use of a (−)-stereoisomer of formula (I) or a pharmaceutically acceptable salt or prodrug thereof to prepare a medicament for treating addiction withdrawal in an animal.

The invention also provides the use of a (−)-stereoisomer of formula (I) or a pharmaceutically acceptable salt or prodrug thereof to prepare a medicament for promoting an antiemetic effect in an animal.

The invention also provides the use of a (−)-stereoisomer of formula (I) or a pharmaceutically acceptable salt or prodrug thereof to prepare a medicament for agonizing a GABA receptor in an animal.

The invention also provides synthetic processes and intermediates disclosed herein that are useful for preparing a (−)-stereoisomer of formula (I) or a salt or prodrug thereof.

DETAILED DESCRIPTION OF THE INVENTION

The present invention provides a (−) stereoisomer of formula (I), or a salt or prodrug thereof as defined hereinabove.

The absolute configuration of such a stereoisomer has been determined to be (R).

In one embodiment, X is H. When X is H, the stereoisomer may also be referred to by the name (R)-(−)-2-sec-butyl-6-isopropylphenol.

Compared with propofol, (R)-(−)-2-sec-butyl-6-isopropylphenol has been found to demonstrate a surprisingly improved overall profile of activity as an anesthetic. More particularly, the compound has been found to produce a more potent effect on anesthetic activity, to exhibit a higher therapeutic index and to retain a comparable pharmacokinetic profile, e.g., exhibit a similar clearance rate. The compound also can produce a less potent effect on mean arterial pressure and heart rate. Furthermore, it is believed that clinical trials will demonstrate that the compound causes less pain on injection than propofol. Injection pain associated with propofol has been correlated to the concentration of propofol in the aqueous phase of its lipid emulsion vehicle. When formulated in identical lipid emulsions, the aqueous phase concentration of (R)-(−)-2-sec-butyl-6-isopropylphenol has been found to be significantly reduced (by more than 70%) compared to propofol.

The other enantiomer of 2-sec-butyl-6-isopropylphenol, (S)-(+)-2-sec-butyl-6-isopropylphenol has also, unexpectedly, been found to demonstrate an improved hemodynamic profile along with similar or improved pharmacological activities, compared to propofol.

Accordingly, compounds according to the invention are particularly useful for inducing or maintaining general anesthesia or promoting sedation in a patient. They are particularly useful for anesthetizing patients having an elevated susceptibility to hemodynamic effects. Such patients include patients suffering from cardiovascular disease such as coronary artery disease, cardiomyopathy, ischemic heart disease, valvular heart disease, and congenital heart disease; patients suffering from chronic hypertension, cerebrovascular disease, or brain injury; patients of an advanced age (for example over 50, 60, 70 or 80 years old); patients with acute blood loss, dehydration, or severe infection including those with hemorrhagic shock, hypovolemic shock, or septic shock; and patients receiving spinal anesthesia, epidural anesthesia, or vasoactive medications; see e.g., Reich D L et al, 2005, Anesth Analg 101, 622. For example, the patient may be one for whom the American Society of Anesthesiologists (ASA) physical status is at least 3. The present invention also contemplates administering the compounds according to the invention to patients that have not been pre-medicated for pain on injection.

As used herein, the term "Pharmaceutically acceptable carrier" includes diluents, adjuvants, excipients or vehicles.

The term "Animal" includes mammals such as, for example, humans, companion animals, zoo animals and livestock.

The term "Treating" a disease or disorder includes 1) ameliorating the disease or disorder (i.e., arresting or reducing the development of the disease or disorder or at least one of the clinical symptoms thereof), 2) ameliorating at least one physical parameter, which may not be discernible by the patient, 3) inhibiting the disease or disorder which can be either physically, (e.g., stabilization of a discernible symptom), physiologically, (e.g., stabilization of a physical parameter) or both, or 4) delaying the onset of the disease or disorder.

Stereoisomeric purity of compounds and prodrugs described herein may be established by conventional analytical methods well known to those of skill in the art. For example, use of chiral NMR shift reagents, gas chromatographic analysis using chiral columns, high pressure liquid chromatographic analysis using chiral columns, polarimetry, isotopic dilution, calorimetry, enzymatic methods, capillary electrophoresis on chiral gels, formation of diastereomeric derivatives through reaction with chiral reagents and conventional analysis via established analytical methods may be used to establish the stereochemical purity of a specific stereoisomer. Alternatively, synthesis using starting materials of known stereochemical enrichment may be used to establish the stereochemical purity of the compounds described herein. Other analytical methods for demonstrating stereochemical homogeneity are known in the field.

The present invention provides a stereoisomer of formula (I) or a salt or prodrug thereof in a non-racemic (i.e., an enantiomerically enriched) form at the center marked by "*" in formula (I). Thus the invention includes a stereoisomer of formula (I) in an enriched mixture that contains no more than 45% of the other enantiomer of that compound of formula (I) that is shown or its salt or prodrug. The (−)-enantiomer isolated in Example 2 below is a specific compound of the invention. In some embodiments of the invention, an enriched mixture contains no more than about 40%, 35%, 30%, 25%, 20%, 15%, 10%, 5%, 4%, 3%, 2%, or 1% of the other enantiomer of a compound of formula (I) or its salt or prodrug. In another embodiment of the invention an enriched mixture contains less than about 1% of the other enantiomer of a compound of formula (I) or its salt or prodrug.

Methods for Preparing a Compound of Formula (I)

Generally, compounds of formula (I) may be prepared by at least three different approaches. In one approach, a racemic mixture is prepared using conventional methods of organic synthesis or purchased from commercial sources and the mixture resolved using methods known to those of skill in the art such as, for example, fractional crystallization, separation on chiral columns, formation of derivatives and separation or kinetic resolution thereof, etc. to provide substantially pure enantiomer of formula (I) or enantiomerically enriched mixtures of compounds of formula (I). Alternatively, asymmetric synthesis may be used to prepare compounds of formula (I). Known chiral precursors can be used to prepare substantially pure enantiomers of formula (I) or enantiomerically enriched mixtures of compounds of formula (I) using known methods. Other methods include preparation of chiral intermediates using, for example, asymmetric hydrogenation, reduction, and/or carbon-carbon bond formation. Also, enzymatic cleavage of prochiral acetate precursors, etc., can be used to produce a compound of formula (I).

Processes for preparing an enantiomerically enriched compound of formula (I) or a salt thereof are provided as further embodiments of the invention and are illustrated by the following procedures.

A compound of formula (I) can be prepared from racemic (I) by employing a chiral auxiliary, crystallographic and/or chromatographic resolution, followed by hydrolysis. In one method, a stereoisomer of formula (I) can be prepared using a chiral isocyanate to form a mixture of carbamate diastereomers that can be separated to yield the desired diastereomer of formula (I) after hydrolysis of the carbamate residue. Specifically, but not limited to, a chiral carbamate derived from R-(+) 1-phenylethylisocyanate can be employed. In another method, a compound of formula (I) can be prepared by diazotizing a chiral aniline. In yet another method, a compound of formula (I) can be prepared by reducing a chiral alkene.

According to another aspect, therefore, the present invention provides a process for preparing a (−) stereoisomer of formula (I) or a salt or prodrug thereof, which comprises:

(a) hydrolysing a carbamic acid (−)-2-sec-butyl-6-isopropylphenyl ester diastereoisomer of formula in which $R^1$ represents a chiral amino group;

(b) diazotizing a corresponding (−)-2-sec-butyl-6-isopropyl aniline of formula or (c) reducing a corresponding 2-(1-methylallyl)-6-isopropylphenol of formula followed if required by forming the free phenol or a salt (such as a pharmaceutically acceptable salt) or pro-drug thereof.

The hydrolysis according to process step (a) may be effected by reacting the carbamate with a base, for example an alkali metal hydroxide, such as potassium or sodium hydroxide, which affords a salt of the (−) stereoisomer of formula (I), such as an alkali metal salt. The free phenol may be obtained by treating this salt with an acid, such as hydrochloric acid. The chiral amino group may be, for example, a chiral 1-arylethylamino group, for example an (R)-1-arylethylamino group such as (R)-1-phenylethylamino.

The carbamate starting material may be prepared by reacting a racemic mixture of the corresponding 2-sec-butyl-6-isopropylphenol with a chiral isocyanate to afford a mixture of diastereoisomers comprising the carbamic acid (−)-2-sec-butyl-6-isopropylphenyl ester diastereoisomer; and separating the corresponding carbamic acid (−)-2-sec-butyl-6-isopropylphenyl ester diastereoisomer of formula (II).

The chiral isocyanate may be, for example, a chiral 1-arylethylisocyanate, for example an (R)-1-arylethylisocyanate such as (R)-(+)-1-phenylethylisocyanate. The resultant product is a mixture of the corresponding 1-arylethylcarbamic acid 2-sec-butyl-6-isopropylphenyl ester diastereoisomers. The desired diastereoisomer can be separated by chromatography using, for example, silica as the stationary phase, or by crystallization.

It has been found, surprisingly, that the use of (R)-(+)-1-phenylethylisocyanate in the above-described method provides a good separation of the stereoisomers of (+)-2-sec-butyl-6-isopropylphenol.

Racemic 2-sec-butyl-6-isopropylphenol may be prepared from 2-isopropyl phenol following the method described in Example 1.

The diazotization process step (b) is conveniently performed by reacting the aniline with an alkali metal nitrite, such as sodium nitrite, in the presence of a copper catalyst, such as $Cu_2O$ with a copper (II) salt, such as copper sulfate.

The chiral aniline of formula (III) may be prepared following the method described in Example 3 herein.

The reduction process step (c) is conveniently performed by hydrogenation in the presence of a group (VIII) metal catalyst, such as palladium on carbon.

Compounds of formula (IV) may be prepared from the racemic phenol, the preparation of which is described in Example 1 herein.

Salts

In cases where compounds are sufficiently acidic, a salt of a compound of formula (I) can be useful as an intermediate for isolating or purifying a compound of formula (I) or an enriched mixture thereof. Additionally, administration of a compound of formula (I) as a pharmaceutically acceptable salt may be appropriate. Examples of pharmaceutically acceptable salts include salts that are obtained using standard procedures well known in the art, for example by reacting a sufficiently acidic compound of formula (I) with a suitable base affording a physiologically acceptable cation. For example, alkali metal (for example, sodium, potassium or lithium) or alkaline earth metal (for example calcium) salts can be made.

Pharmaceutical Compositions

The pharmaceutical compositions disclosed herein comprise a compound of formula (I) disclosed herein with a suitable amount of a pharmaceutically acceptable carrier, so as to provide a form for proper administration to a patient. The compounds of formula (I) may be formulated as pharmaceutical compositions and administered to a patient, in a variety of forms adapted to the chosen route of administration, i.e., orally, parenterally, intravenously, intramuscularly, topically or subcutaneously.

Thus, the compounds of formula (I) can be systemically administered in combination with pharmaceutically acceptable carriers such as inert diluents or edible carriers. Such compositions and preparations may contain at least 0.1% of active compound. The percentage of the compositions and preparations can, of course, be varied and can conveniently be between about 0.1% to about 60% of the weight of a given unit dosage form. The amount of active compound in such therapeutically useful compositions is such that an effective dosage level is obtained.

The compounds of formula (I) described herein are typically formulated as pharmaceutical compositions suitable for intravenous administration. The compounds of formula (I) may be relatively insoluble in water. Thus, for intravenous administration, the compounds of formula (I) are typically formulated in aqueous media using one or more water-immiscible solvents and one or more emulsifiers or surfactants. Individual formulations can include one or more additional components such as stabilizers, tonicity modifiers, bases or acids to adjust pH and solubilizers. The formulations may also optionally contain a preservative, such as, for example, ethylenediaminetetraacetic acid (EDTA) or sodium metabisulfite. Useful oil-in-water emulsions that contain a preservative such as EDTA that may be used in conjunction with compounds described herein are described in U.S. Pat. Nos. 5,908,869, 5,714,520, 5,731,356 and 5,731,355.

A wide range of water-immiscible solvents can be used in the pharmaceutical compositions described herein. The water-immiscible solvent can be a vegetable oil, such as, for example, soybean, safflower, cottonseed, corn, sunflower, arachis, castor or olive oil.

Alternatively, the water-immiscible solvent may be an ester of a medium or long-chain fatty acid, such as, for example, a mono-, di-, or triglyceride, an ester of a combination of a medium and long-chain fatty acid or a chemically modified or manufactured material such as ethyl oleate, isopropyl myristate, isopropyl palmitate, a glycerol ester, polyoxyl or hydrogenated castor oil. The water-immiscible solvent can also be a marine oil, such as, for example cod liver or another fish-derived oil. Other suitable solvents include fractionated oils, such as, for example, fractionated coconut oil or modified soy bean oil. The water-immiscible solvent may include "structured lipids." (see, e.g., Lipid Biotechnology, T. M. Kuo and H. W. Gardner (eds.), Marcel Dekker, Inc. New York, N.Y.). Many structured lipids are available from commercial suppliers such as Danisco A/S, Copenhagen Denmark and S&J Lipids, Ostrander, Ohio.

The pharmaceutical compositions described herein can also contain an emulsifier. Suitable emulsifiers include synthetic non-ionic emulsifiers, such as, for example, ethoxylated ethers, ethoxylated esters, polyoxypropylene-polyoxyethylene block co-polymers and phospholipids. Naturally-occurring phospholipids, such as egg or soya phospholipids, and modified or artificially manipulated phospholipids or mixtures thereof can also be used. In some embodiments, emulsifiers are egg phospholipids and soya phospholipids. Egg yolk phospholipids include phosphatidylcholine, lecithin and phosphatidylethanolamine.

The pharmaceutical formulations described herein can comprise a lipid emulsion comprising from about 0.1% to about 5% (w/w) of a formula (I) compound, from about 5 to about 25% (w/w) water immiscible solvent and from about 40% to about 90% (w/w) water. A preferred formulation comprises from about 0.5% to about 2% (w/w) of a formula (I) compound. In one embodiment, a pharmaceutical formulation comprises from about 0.5% to about 5% (w/w) of a formula (I) compound and from about 0% to about 50% (w/w) of a water immiscible solvent.

The pharmaceutical formulations described herein may also include stabilizing agents. Anionic stabilizers include, for example, phosphatidylethanolamines, conjugated with polyethylene glycol, (PEG-PE) and phosphatidylglycerols, a specific example of which is dimyristolphosphatidylgylcerol (DMPG). Additional stabilizers include, but are not limited to, oleic acid and its sodium salt, cholic acid and deoxycholic acid and respective salts thereof, cationic lipids such as stearylamine and oleylamine, and 3|3-[N-(N',N'-dimethylaminoethane)carbamoyl]cholesterol (DC-Chol).

The pharmaceutical compositions described herein can be made isotonic with blood by the incorporation of a suitable tonicity modifier. Glycerol is most frequently used as a tonicity modifier. Alternative tonicity modifying agents include xylitol, mannitol and sorbitol. The pharmaceutical compositions are typically formulated to be at physiologically neutral pH, typically in the range 6.0-8.5. The pH can be adjusted by the addition of base, for example, NaOH or $NaHCO_3$, or in some cases acid, such as HCl.

The compounds of formula (I) can be formulated with pharmaceutically safe oil-water emulsions comprising a vegetable oil, a phosphatide emulsifier, typically egg lecithin or soybean lecithin, and a tonicity modifier such as, for example, Liposyn® II and Liposyn® III (Abbott Laboratories, North Chicago, Ill.) and Intralipid® (Fresenius Kabi AB, Uppsala, Sweden) or other similar oil-water emulsions.

Compounds of formula (I) can also be formulated in a triglyceride comprising esters of at least one medium chain length ($C_6$-$C_{12}$) fatty acid. In some embodiments, the triglyceride is an ester of a $C_8$-$C_{10}$ fatty acid. Triglycerides suitable for formulating compounds of formula (I) include, but are not limited to, Miglyol® (Condea Chemie GmbH (Witten, Germany). For example, Miglyol® 810 or 812 (caprylic ($C_{10}$)/capric ($C_8$) glyceride) is useful for formulation of compounds of Formula (I).

Additionally, compounds of formula (I) described herein can be formulated analogously to pharmaceutical compositions of propofol as described, for example, in U.S. Pat. Nos. 4,056,635, 4,452,817 and 4,798,846.

Still other suitable formulations for use in the present invention can be found, for example in Remington's Pharmaceutical Sciences, Philadelphia, Pa., 19th ed. (1995).

Therapeutic/Prophylactic Administration and Doses.

A compound of formula (I) and/or pharmaceutical compositions thereof may be administered alone or in combination with other pharmaceutical agents including compounds disclosed herein and/or pharmaceutical compositions thereof. The compounds disclosed herein may be administered or applied per se or as pharmaceutical compositions. The specific pharmaceutical composition depends on the desired mode of administration, as is well known to the skilled artisan.

Compounds disclosed herein and/or pharmaceutical compositions thereof may be administered to a subject by intravenous bolus injection, continuous intravenous infusion, oral tablet, oral capsule, oral solution, intramuscular injection, subcutaneous injection, transdermal absorption, buccal absorption, intranasal absorption, inhalation, sublingually, intracerebrally, intravaginally, rectally, topically, particularly to the ears, nose, eyes, or skin or any other convenient method known to those of skill in the art. In some embodiments, compounds disclosed herein and/or pharmaceutical compositions thereof are delivered via sustained release dosage forms, including oral sustained release dosage forms. Administration can be systemic or local. Various delivery systems are known, (e.g., encapsulation in liposomes, microparticles, microcapsules, capsules, "patient controlled analgesia" drug delivery systems, etc.) that can be used to deliver compounds disclosed herein and/or pharmaceutical compositions thereof.

The amount of compounds disclosed herein and/or pharmaceutical compositions thereof that will be effective can be determined by standard clinical techniques known in the art. The amount of compounds disclosed herein and/or pharmaceutical compositions thereof administered will, of course, be dependent on, among other factors, the subject being treated, the weight of the subject, the age of the subject, the condition of the subject, the intended effect of the compounds, the manner of administration and the judgment of the prescribing physician. For example, the dosage level of a (R)-(–) or (–) stereoisomer of formula I for producing general anesthesia may be in the range of from about 1 to about 10 mg/kg. Preferred induction doses range from about 1 to about 3 mg/kg. Preferred maintenance doses range from about 1 to about 20 mg/kg/hr. Preferred doses to produce a sedative effect range from about 0.3 to about 8 mg/kg/hr.

Combination Therapy

In certain embodiments, compounds disclosed herein and/or pharmaceutical compositions thereof can be used in combination therapy with at least one other therapeutic agent. The compounds disclosed herein and/or pharmaceutical compositions thereof and the therapeutic agent can act additively or, more preferably, synergistically. In some embodiments, compounds disclosed herein and/or pharmaceutical compositions thereof are administered concurrently with the administration of another therapeutic agent such as, for example, other sedative hypnotic agents (e.g., etomidate, thiopental, midazolam, dexmedetomidine, ketamine), anesthetic agents (e.g., desflurane, sevoflurane, isoflurane, nitrous oxide), analgesics (e.g., an opioid such as remifentanil, morphine, meperidine, hydromorphone, methadone, fentanyl, sulfentanil, or alfentanil, or a non-opioid analgesic such as ketorolac, gapapentin, lidocaine, or ketamine), paralytic agents, such as rocuronium, cis-atracurium, vecuronium, or pancuronium bromide, antiemetics (e.g., ondansetron, dolasetron, droperidol), cardiovascular agents (e.g., metoprolol, propranolol, esmolol, clonidine, phenylephrine, ephedrine, epinephrine, norepineprine, dopamine, diltiazem, atropine, glycopyrrolate, lisinopril, nitroglycerin, sodium nitroprusside, digoxin, milrinone), steroids (e.g., dexamethasone, hydrocortosone, methylprednisolone), anti-infective agents (e.g., cefazolin, vancomycin), diuretics (e.g., furosemide, hydrochlorothiazide, spironolactone), mood altering medications (e.g., fluoxetine, aripiprazole), or stimulants such as nicotine or cytisine.

For example, compounds disclosed herein and/or pharmaceutical compositions thereof may be administered together with other therapeutic agents. In other embodiments, compounds disclosed herein and/or pharmaceutical compositions thereof are administered prior or subsequent to administration of other therapeutic agents.

Prodrugs

The term "prodrug" as used herein refers to a compound that can be metabolized or converted in vivo to provide a compound of formula (I). Typically, prodrugs include compounds that are prepared by modifying the phenol group in a compound of formula (I) to provide a corresponding compound that can be metabolized or converted in vivo to provide the corresponding compound of formula (I). Prodrugs of phenolic compounds as well as methods for their preparation have been reported. For example, see U.S. Patent Application Publication Numbers 20070015716, 20060287525, 20060205969, 20060041011, 20050239725, and 20050107385.

Other suitable prodrug groups are discussed in the following Published International Patent Applications and Published US Patent Applications: WO 2005023204; US 2005107385; US 2005004381; WO 2004092187; WO 2004032971; US 2006100163; WO 2006033911; WO 2004033424; US 2005267169; WO2003086413; US 2002370213; WO 2003057153; US 2001342755; US 2002099013; WO 2002034237; US 2004127397; WO 2002013810; WO 2000048572; US 2006166903; WO 200008033; US 2001025035; WO 9958555; and US 199875356; and in the other following publications: Krasowski, M. D. Current Opinion in Investigational Drugs (Thompson Scientific) (2005) 6(1), 90-98; Fechner, J. et al., *Anesthesiology*, 2004, 101, 3, 626-639; Altomare C. et al., *European Journal of Pharmaceutical Sciences;* 2003, 20, 1, 17-26; Sagara, Y. et al., *Journal of Neurochemistry;* 1999; 73, 6, 2524-2530, and Trapani, G., et al., *International Journal of Pharmaceuticals,* 1998, 175, 2, 195-204.

As described hereinabove, the other enantiomer of 2-sec-butyl-6-isopropylphenol, (S)-(+)-2-sec-butyl-6-isopropylphenol, has also been found to demonstrate an improved hemodynamic profile along with a similar or improved pharmacological activity, compared to propofol. Accordingly, the present invention also provides this isomer, its para-fluoro derivative and pharmaceutically acceptable salts and prodrugs thereof, and pharmaceutical compositions thereof, for use as anesthetics.

The (S)-(+) or (+) stereoisomers of formula (I), their salts and prodrugs thereof may each be prepared following the general methods described for the preparation of the corresponding (−) stereoisomers. For example, the (S)-(+) or (+) stereoisomer of 2-sec-butyl-6-isopropylphenol may be prepared by reacting a racemic mixture of the corresponding 2-sec-butyl-6-isopropylphenol with a chiral isocyanate to afford a mixture of carbamate diastereomers that can be separated to yield the desired diastereomer of formula (I) after hydrolysis of the carbamate residue. For the preparation of the (S)-(+) or (+) stereoisomer, a (S)-1-arylethylisocyanate such as (S)-(+)-1-phenylethylisocyanate can advantageously be used. Accordingly, the present invention also provides a carbamic acid (S)-2-sec-butyl-6-isopropylphenyl ester diastereoisomer of formula (II), in which $R^1$ represents a chiral amino group, such as an (S)-1-arylethylamino group. All of the stereoisomers may be separated from the racemic compound by chiral phase chromatography, for example as described in Example 2 herein.

The (S)-(+) or (+) stereoisomers of formula (I) may exist, be formulated and be administered to patients as described and exemplified herein for the (R)-(−) or (−) stereoisomers. For the (S)-(+) or (+) stereoisomers, the dosage level for producing general anesthesia may be in the range of from about 1 to about 12 mg/kg. Preferred induction doses range from about 1.2 to about 4 mg/kg. Preferred maintenance doses range from about 1.5 to about 30 mg/kg/hr. Preferred doses to produce a sedative effect range from about 0.5 to about 12 mg/kg/hr.

The invention will now be illustrated by the following non-limiting Examples.

The ability of a compound of the invention to produce a sedative or hypnotic effect can be determined using standard pharmacological models which are well known to the art. The hypnotic potency of a compound of the invention was demonstrated using a loss of righting reflex assay in the rat (as described in Test A below). The potency of a compound of the invention was compared to the potency of propofol using this assay.

Test A. Loss of Righting Reflex Assay

Male Sprague Dawley rats were restrained in a holder and injection test compounds were injected in the tail vein (based on mg test compound/kg body weight). Following administration, the rats were placed in dorsal recumbent position on a heating blanket. The time to onset for the loss of the Righting Reflex (RR-ability of rat to right itself) was recorded, as was the duration of the loss of the RR. The compound of formula (I) prepared in example 2 was found to be more potent than propofol in Test A. Rats administered a 7 mg/kg bolus of 1%-formulated (R)-(−)-2-sec-butyl-6-isopropylphenol exhibited 14.9 minutes of anesthesia compared to 7.1 minutes for rats administered the same dose and formulation of 1% propofol.

The hemodynamic profile of a compound of the invention can be determined using standard pharmacological models which are well known to the art. The hemodynamic and anesthetic profiles of a compound of the invention were evaluated simultaneously using an anesthetized pig model (as described in Test B below). In this assay, the hemodynamic profile of a compound of the invention was compared to that of propofol at equi-anesthetic doses.

Test B. Anesthetized Pig Model

The anesthetic induction will be performed using a modification of a technique described by Ko et al (Ko et al., Lab Anim Sci 1993; 43: 476-80) for swine (Telazol, xylazine and ketamine given as an intramuscular injection). The minimal effective dose for induction and tracheal intubation will be used. When the animal is recumbent, oxygen will be administered by mask at 8 mL/min and an IV will be started in an ear vein running normal saline at 70 mL/hr. The pig's trachea will be intubated and mechanically ventilated to maintain arterial $P_{CO2}$ at approximately 35 mmHg.

ECG electrodes will be placed using a lead II configuration to monitor cardiac activity. An arterial catheter will be placed in the right femoral artery to monitor blood pressure. A pulmonary artery catheter will be placed via the right jugular vein for measuring cardiac output, pulmonary capillary wedge pressure, and central venous pressure. A catheter will also be placed in the abdominal aorta via the left femoral artery for blood sampling.

Bipolar electroencephalograph leads will be placed using low impedance surface electrodes placed over the frontal and occipital regions of the cerebral hemispheres, approximately 50 mm apart and 20 mm from the midline. A ground electrode will be placed midline between the frontal and occipital regions. Alternatively, an integrated electrode sensor array (Aspect Medical) compatible with an electroencephalogram analyzer (Aspect Medical) may be applied. Anesthesia will be maintained with isoflurane adjusted to keep the mean arterial blood pressure at 100 mmHg during the stabilization period and intravenous pancuronium will be administered as needed for muscle relaxation.

After the initial animal instrumentation is complete, (usually requiring approximately 2-3 hours), an additional 1 hour and 15 minutes will serve as a period of stabilization and baseline data gathering (and to ensure near complete dissipation of the effects of the anesthetic induction drugs). Isoflurane inhalation may be continued throughout the study or stopped, and the isoflurane allowed to "wash-out" for 15 mins prior to the administration of test compound.

The agent or propofol will be administered intravenously by a 20 minute infusion after the stabilization period through the peripheral IV catheter. A pilot dose-finding study will be performed to establish an appropriate infusion dose for each agent. In this pilot study, multiple doses (up to 5 infusions in total) may be administered to each pig with at least 90 minutes between doses. Blood samples (1 mL each) may be collected at pre-dose and at 2, 4, 6, 8, 10, 12, 15, 20, 22, 22, 25, 35, 50, 65 and 80 minutes after the start of the first infusion for pharmacokinetic purposes; EEG will be recorded continuously as the primary pharmacodynamic endpoint.

Arterial blood samples (1 mL each) will be taken from the abdominal aorta at 2, 4, 6, 8, 10, 11, 12, 13, 14, 15, 17.5, 20, 25, 30, 45, 60, 90, 120 and 180 minutes after the start of the infusion. A control sample prior to the start of the infusion will also be taken.

The EEG signal will be fed to a BIS analyzer (Aspect Medical) which provides continuous output of processed EEG data. The output consists of a "BIS" number calculated by a proprietary algorithm that ranges between 100 (fully conscious) and 0 (isoelectric) and indicates brain activity.

Hemodynamic data will be recorded and plotted to assess trends over the drug exposure period. Data for each agent will be compared to propofol for effects on BIS, heart rate (HR), mean arterial blood pressure (MAP) and cardiac output.

Figure 1:
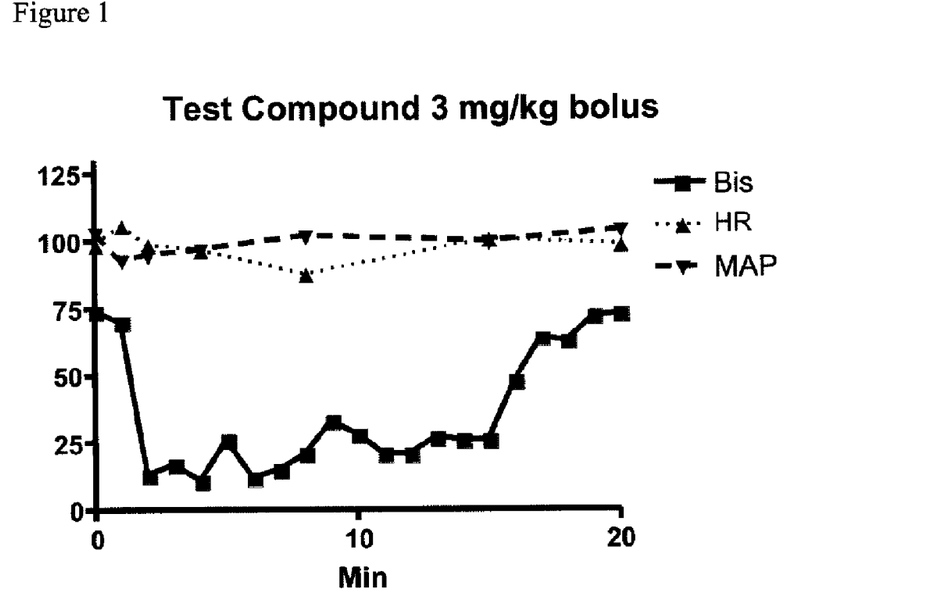
FIG. 1 shows the hemodynamic effects of the (−) stereoisomer of formula (I) in which X is H dosed at 3 mg/kg in a pig study.
Figure 2:
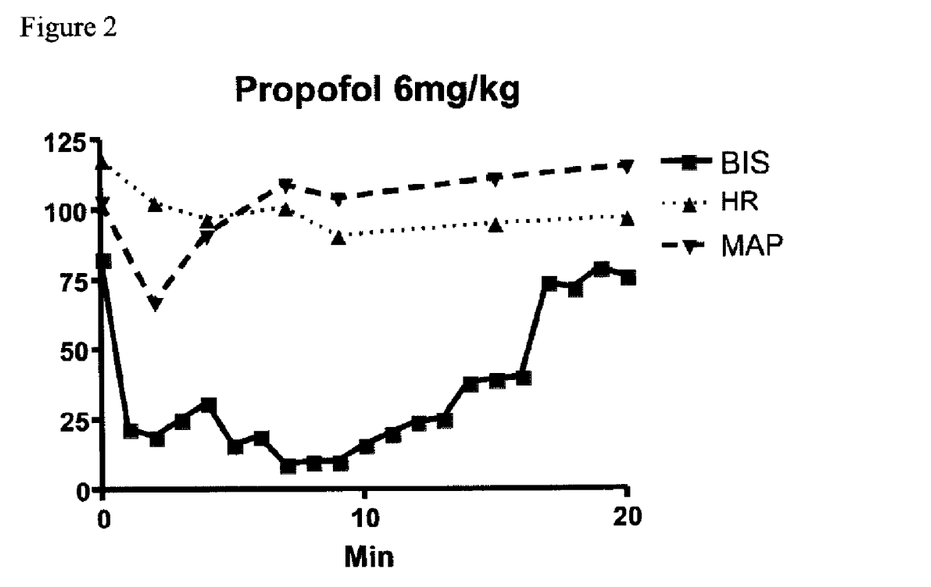
FIG. 2 shows the hemodynamic effects of propofol dosed at 6 mg/kg in a pig study.

Hemodynamic data for (R)-(-)-2-sec-butyl-6-isopropylphenol (Test Compound), prepared as described in Example 2, and for propofol are shown in FIGS. 1 and 2 respectively. The data demonstrate that this compound of the invention exhibits an improved hemodynamic profile (specifically with respect to hypotension) vs. propofol at equi-anesthetic doses.

EXAMPLES

Example 1

Synthesis of Racemic 2-sec-butyl-6-isopropylphenol (Compound c)

Synthesis of allyl ether (a): To a solution of dry $CH_2Cl_2$ (40 L) in a reactor (~200 L capacity) was added 2-isopropyl phenol (2.5 Kg, 18.38 mol). The mixture was cooled to 0° C. to −10° C. Crotyl alcohol (1.9 L, 22 mol) was added to the reaction mixture, followed by the addition of triphenylphosphine (6 Kg, 22 mol) portion-wise over 5 hours. To this was added DIAD (4.5 L, 22.1 mol) dropwise over a period of 4 hours. The mixture was brought to room temperature and stirred overnight. After the disappearance of the starting material as judged by TLC, the mixture was diluted with dichloromethane (25 L), and washed with water (50 L×2) and brine (504 The organic layer was dried over anhydrous $Na_2SO_4$ (5 Kg), filtered and concentrated to dryness. Petroleum ether (50 L) was then added and the mixture stirred at room temperature for 1 hour. The precipitated white solid (triphenylphosphine oxide) was filtered off and washed with petroleum ether (10 L×2). The combined filtrate (~80 L) was concentrated to obtain a yellow viscous liquid (~5 Kg). This crude material was purified by silica gel (60-120 mesh, ~30 Kg) column chromatography using 5% ethyl acetate in petroleum ether as the eluting solvent. Pure fractions were combined and the solvents were concentrated to afford 1.5 Kg (43%) of pure material.

Synthesis of homostyrylphenol (b): Allyl ether a (250 g, 1.28 mol) was heated at 270° C. under a nitrogen atmosphere for about 25 hours. The reaction mixture was then diluted with EtOAc (2 L) and washed with water (3 L) and brine (1 L). It was dried over anhydrous $Na_2SO_4$ (100 g), filtered and evaporated to dryness to afford 240 g of product.

Synthesis of 2-sec-butyl-6-isopropylphenol (c): To a solution of compound b (500 g, 2.57 mol) in dry MeOH (5 L) at 0° C. was added Pd\C (50 g, 10 mol %). The mixture was then hydrogenated in an autoclave under 5 Kg of hydrogen pressure overnight. The reaction mixture was then filtered through Celite® and evaporated to afford 400 g of the crude product which was purified by silica gel column chromatography using 2% ethyl acetate in petroleum ether as the eluting solvent. Purified fractions were combined and concentrated to afford 273 g of product.

Example 2

Crystallographic Resolution of Racemic 2-sec-butyl-6-isopropylphenol via Chiral Carbamate Formation to Provide a Stereoisomer of Formula (I)

3
stereoisomer of Formula (I)
(−) 2-sec-butyl-6-isopropylphenol

Synthesis of R-(+)-1-Phenyl-ethyl)carbamate of racemic 2-sec-butyl-6-isopropylphenol (1a): A mixture of racemic 2-sec-butyl-6-isopropylphenol (1.92 g, 10 mmol), R-(+)-1-phenylethylisocyanate (1.47 g, 10 mmol), and 4-(dimethylamino)pyridine (0.06 g, 0.5 mmol) was heated at 80° C. in dry pyridine (10 ml) overnight. The reaction mixture was concentrated on a rotary evaporator. The resulting residue was then partitioned between ethyl acetate (75 ml) and 1M HCl aq (100 ml) in a separatory funnel. The organic layer was washed with 1M HCl aq (2×100 mL), brine (100 ml), then dried over anhydrous $MgSO_4$. Filtration and subsequent evaporation of the solvent provided carbamate (1) (3.1 g, 90%) as a solid.

(−)-2-sec-Butyl-6-isopropylphenol (3): R-(+)-(1-phenyl)ethylcarbamate of 2-sec-butyl-6-isopropylphenol (1) (100 g, 294 mmol) was dissolved in ~2.5 L hot hexanes. The solution was kept at room temperature for 24-48 hours to allow for complete crystallization. The resulting crystals were filtered and washed with cold hexanes (~200 ml). This procedure was repeated 7 times (with concurrent decrease of hexanes volumes). The crystals were dried under vacuum to afford crystalline diastereomerically enriched R-(+)-1-phenyl-ethyl)-carbamate of 2-sec-butyl-6-isopropylphenol (17 g, 34%). The resulting carbamate mixture was hydrolyzed at 100° C. in a 1:1 mixture of dioxane: 1M NaOH aq. for 1-2 min. The reaction mixture was then diluted with ether, neutralized with dilute HCl aq. and washed with brine. The ether layer was then dried over anhydrous $MgSO_4$, filtered and evaporated to yield (−)-2-sec-butyl-6-isopropylphenol (9.6 g, ~100%).

Vacuum distillation (~1-2 mm) was performed. Fractions (105-110° C.) were collected to afford (3), (−)-2-sec-butyl-6-isopropylphenol (7.5 g, 78%, 19:1 enantiomeric ratio as determined by chiral HPLC). Optical rotation: $\alpha^{20}_D = -7.16°$. $^1$H NMR (250 MHz, chloroform-d1) δ 0.84-0.90 (t. 3H), δ 1.21-1.26 (m. 11H), δ 2.85-2.89 (m. 1H), δ 3.11-3.16 (m. 1H), δ 4.74 (s, 1H), δ 6.87-6.90 (t, 1H) δ 6.987-7.05(m 2H).

Analysis of optical purity by chiral chromatography: Analyses R (+)-(1-phenyl)ethylcarbamate of 2-sec-butyl-6-isopropylphenol (1) were performed on CHIRALCEL OD-H column (4.6×250 mm) in isocratic mode, mobile phase—n-hexanes containing 1% isopropanol, flow rate 1 ml/min, 20 min, detection 270 nm. Samples were dissolved in hexanes.

Synthesis of S-(−)-1-Phenyl-ethyl)-carbamate of racemic 2-sec-butyl-6-isopropylphenol (1b): A mixture of racemic 2-sec-butyl-6-isopropylphenol (1.92 g, 10 mmol), S-(−)-1-phenylethylisocyanate (1.47 g, 10 mmol), and 4-(dimethylamino)pyridine (0.06 g, 0.5 mmol) was heated at 80° C. in dry pyridine (10 ml) overnight. The reaction mixture was concentrated on a rotary evaporator. The resulting residue was then partitioned between ethyl acetate (75 ml) and 1M HCl aq (100 ml) in a separatory funnel. The organic layer was washed with 1M HCl aq (2×100 mL), brine (100 ml), then dried over anhydrous $MgSO_4$. Filtration and subsequent evaporation of the solvent provided carbamate (1b) as a solid.

(+)-2-sec-Butyl-6-isopropylphenol (3): S-(−)-(1-phenyl)ethylcarbamate of 2-sec-butyl-6-isopropylphenol (1b) (100 g, 294 mmol) was dissolved in ~2.5 L hot hexanes. The solution was kept at room temperature for 24-48 hours to allow for complete crystallization. The resulting crystals were filtered and washed with cold hexanes (~200 ml). This procedure was repeated 7 times (with concurrent decrease of hexanes volumes). The crystals were dried under vacuum to afford crystalline diastereomerically enriched S-(−)-1-phenyl-ethylcarbamate of 2-sec-butyl-6-isopropylphenol. The resulting carbamate mixture was hydrolyzed at 100° C. in a 1:1 mixture of dioxane:1M NaOH aq. for 1-2 min. The reaction mixture was then diluted with ether, neutralized with dilute HCl aq. and washed with brine. The ether layer was then dried over anhydrous $MgSO_4$, filtered and evaporated to yield enantiomerically enriched 2-secbutyl-6-isopropylphenol. Vacuum distillation (~1-2 mm) was performed. Fractions (105-110° C.) were collected to afford (3), enantiomerically enriched 2-sec-butyl-6-isopropylphenol (19:1 enantiomeric ratio as determined by chiral HPLC). Optical rotation: $\alpha^{20}_D$=+5.95°. 1H NMR (250 MHz, chloroform-d1) δ 0.84-0.90 (t. 3H), δ 1.21-1.26 (m. 11H), δ 2.85-2.89 (m. 1H), δ 3.11-3.16 (m. 1H), δ 4.74 (s, 1H), δ 6.87-6.90 (t, 1H) δ 6.987-7.05(m 2H).

Example 3

(−)-2-sec-butyl-6-isopropylphenol via (−)-2-sec-butylaniline 1. enatiomerically enriched 2-sec-butylaniline 4. stereoisomer of Formula (I). (-)-2-sec-butyl-6-isopropylphenol Crystallographic resolution (−)-2-sec-butylaniline (1): 2-Sec-butylaniline (1.49 g, 10 mmol) and (S)-(+)-mandelic acid (1.52 g, 10 mmol) were dissolved in 20 ml ether with gentle heating. The solution was cooled to 4° C. and kept at 4° C. for 2 hr. Crystalline material was filtered, washed with cold ether and dried (1.5 g, 50%). The salt was recrystallized from ethyl acetate-hexane (1 g, 33%, 19:1 isomer's ratio). Optical purity of 2-sec-butylaniline was determined by chiral chromatography. (−)-2-sec-butylaniline (1) was extracted by treatment of an ether solution of the salt with 1M NaOH (0.4 g, 26.5%).

Analysis of optical purity by chiral chromatography: Analyses 2-sec-butylanilines were performed on CHIRALCEL OD-H column (4.6×250 mm) in isocratic mode, mobile phase—n-hexanes containing 1% isopropanol, flow rate 1 ml/min, 20 min, detection 270 nm. Samples were dissolved in hexanes. Mandelic acid salts were preliminary treated with a mixture of hexanes and 3M NaOH aq. The hexanes layer was directly loaded on to column.

Synthesis of (−)-2-sec-butyl-6-bromoaniline (2): (−)-2-Sec-butylaniline (1) (6.7 g, 45 mmol) was dissolved in 240 ml benzene followed by the addition of N-bromosuccinimide (8 g, 45 mmol). The reaction mixture was stirred at room temperature overnight. The solvent was then removed under reduced pressure. The desired product was purified by silica gel chromatography (CombiFlash, 120 g column, hexane-DCM). Fractions 1-3.1 g (30%, pure (−)-2-sec-butyl-4-bromoaniline), fractions 2-6.2 g (60% mixture of (−)-2-sec-butyl-6-bromo- and (+2-sec-butyl-4,6-dibromoanilines). Fraction 2 was distilled and ((−)-2-sec-butyl-6-bromoaniline was collected 115-127° C., at 5 mm) (4.9 g, 48%).

Synthesis of (−)-2-sec-butyl-6-isopropylaniline (3): (−)-2-Sec-butyl-6-bromoaniline (2) (0.684 g, 3 mmol), isopropenylboronic acid pinacol ester (1 g, 6 mmol), tetrakis(triphenylphosphine)palladium(0) (0.035 g, 0.03 mmol), MeCN 10 ml and $K_2CO_3$ (5 ml, 1M solution) were heated in a microwave at 160° C. for 400 sec. The reaction mixture was diluted with water (75 ml). Products were extracted with ethyl acetate (50 ml). The organic layer was washed with 5% $NaHCO_3$, brine and dried over anhydrous $MgSO_4$. The solvent was removed under reduced pressure, and the compound purified by silica gel chromatography (CombiFlash, 30 g column, hexane-ethyl acetate). The reduction was then performed in MeOH (40 ml) over 5% Pd/C (~0.3 g), hydrogen pressure 60 psi overnight (0.48 g, 72%).

Synthesis of (−)-2-sec-butyl-6-isopropylphenol (4): (−)-2-Sec-butyl-6-isopropylaniline (3) (1.92 g, 10 mmol) was dissolved in 20 ml 15% $H_2SO_4$ at 60° C., and then cooled to 0° C. A solution of $NaNO_2$ (0.76 g, 11 mmol) in 8 ml water was added to the reaction mixture rapidly (~30 sec) with vigorous stirring keeping temperature below 0° C. The solution was stirred for an additional 2 minutes, and then added in one portion to the suspension of $Cu_2O$ (1.5 g), in aqueous $CuSO_4$× $5H_2O$ (10 g in 220 ml) with vigorous stirring at 50° C. Reaction mixture was stirred 30 min. and cooled to room temperature. The reaction was repeated five times with the same scale (total 9.13 g of aniline was used), and all reaction mixtures were combined. Organic material was extracted twice with ether (400 ml). The solvent was evaporated, and the compound purified by silica gel chromatography. CombiFlash chromatography (Hexane/EtAc) was performed and final product distilled (105-110*C/~3 mm) (4.1 g (45%). Optical rotation: $\alpha^{20}_D$=−7.58° (c=5, pentane). 1H NMR (250 MHz, chloroform-d1) δ 0.84-0.90 (t. 3H), δ 1.21-1.26 (m. 11H), δ 2.85-2.89 (m. 1H), δ 3.11-3.16 (m. 1H), δ 4.74 (s, 1H), δ 6.87-6.90 (t, 1H) δ 6.987-7.05(m 2H).

Example 4

Formulation

The following illustrates a representative dosage form containing a compound of formula (I) for therapeutic use.

| Ingredient | Batch Weight | w/w % |
|---|---|---|
| Soybean Oil | 70 g | 11.71 |
| Soybean Phospholipids (Lipid S-75) | 8.4 g | 1.41 |
| Compound of formula (I) | 3.5 g | 0.59 |
| Glycerine | 15.75 g | 2.64 |
| Disodium Edetate | 0.035 g | 0.01 |
| Sodium Hydroxide (pH adjustment) | | |
| Subtotal | 97.685 | |
| Sterile Water For Injection | 500 mL | 83.66 |
| Total | 597.685 | 100 |

Example 5

Formulation

The following illustrates a representative dosage form containing a compound of formula (I) for therapeutic use.

| Ingredient | Batch Weight | w/w % |
|---|---|---|
| Soybean Oil | 70 g | 11.66 |
| Soybean Phospholipids (Lipid S-75) | 8.4 g | 1.40 |
| Compound of formula (I) | 6.0 g | 1.00 |
| Glycerine | 15.75 g | 2.62 |
| Disodium Edetate | 0.035 g | 0.01 |
| Sodium Hydroxide (pH adjustment) | | |
| Subtotal | 100.185 | |
| Sterile Water For Injection | 500 ml | 83.31 |
| Total | 600.185 | 100 |

Example 6

Formulation

The following illustrates a representative dosage form containing a compound of formula (I), for therapeutic use.

| Ingredient | Batch Weight | w/w % |
|---|---|---|
| Soybean Oil | 70 g | 11.72 |
| Soybean Phospholipids (Lipid S-75) | 8.4 g | 1.41 |
| Compound of formula (I) | 3.0 g | 0.50 |
| Glycerine | 15.75 g | 2.64 |
| Disodium Edetate | 0.035 g | 0.01 |
| Sodium Hydroxide (pH adjustment) | | |
| Subtotal | 97.185 | |
| Sterile Water For Injection | 500 ml | 83.73 |
| | 597.185 | 100 |

Biological Tests

The pharmacological profile of (R)-(−)-2-sec-butyl-6-isopropylphenol was evaluated in comparison with propofol in the tests described in the following Examples. In these Examples, (R)-(−)-2-sec-butyl-6-isopropylphenol is referred to as Compound 1.

Example 7

Pain on Injection—Aqueous Phase Concentration

Injection pain, a common problem of propofol administration, is thought to be caused by propofol present in the aqueous phase of the lipid emulsion (see, e.g., Klement W et al, 1991, Br J Anaesth 67, 281). Several studies have reported a significant decrease in pain on injection when the aqueous phase concentration of propofol is reduced compared to the amount of propofol in the aqueous phase of DIPRIVAN (see, e.g., Doenicke A W et al, 1996, Anesth Analg 82, 472; Ueki R et al, 2007, J Anesth 21, 325).

The concentration of Compound 1 in the aqueous phase (aqueous phase concentration) of a lipid emulsion formulation was determined. This aqueous phase concentration was compared to that of propofol formulated in the same formulation and to that of DIPRIVAN® (AstraZeneca, Wilmington, Del., USA).

A one percent (1%) Compound 1 formulation was formulated in accordance with Example 5, Compound 1 being prepared as described in Example 2. A 1% propofol formulation was formulated in the same manner. DIPRIVAN (1% propofol injectable emulsion) was used as purchased from AstraZeneca.

The aqueous phase concentrations of Compound 1 and propofol were determined using the ultrafiltration method described by Teagarden D L at al., 1988, Pharmaceutical Research 5, 482. Briefly, four 0.4-ml samples of the 1% Compound 1 formulation, four 0.4-ml samples of the 1% propofol formulation, and two 0.4 samples of DIPRIVAN were placed in Ultrafree®-MC microcentrifuge filters (Millipore, Billerica, Mass.) and the aqueous phases separated from the lipid phases by microcentrifugation for 15 min at 5000 rpm. The concentrations of Compound 1 and propofol in the respective aqueous phases were quantified by liquid chromatography tandem mass spectrometry (LC/MS/MS) against standard curves of Compound 1 and propofol using thymol as an internal reference standard (analyses performed by Alturas Analytics, Inc., Moscow, Id.).

The aqueous phase concentration of Compound 1 in the 1% Compound 1 formulation was 1.78±0.17 µg/ml. The aqueous phase concentration of propofol in the 1% propofol formulation was 6.28±0.41 µg/ml. The aqueous phase concentration of propofol in DIPRIVAN was 4.1 µg/ml.

These results demonstrated a 72% reduction in the aqueous phase concentration of Compound 1 compared to that of propofol in identical formulations, and a 57% reduction in the aqueous phase concentration of Compound 1 compared to that of propofol in DIPRIVAN.

Example 8

Pharmacokinetic Studies

Pharmacokinetic (PK) studies were conducted in domestic pigs to evaluate the pharmacodynamic effects of Compound 1 and to compare such effects to those of propofol.

A 0.5% Compound 1 formulation, prepared as described in Example 2 and formulated in accordance with Example 6, was administered to 6 pigs via a 20-min intravenous (IV) infusion at 0.6 mg/kg/min (12 mg/kg total dose). Plasma concentrations of Compound 1 were compared to historical propofol data generated per a similar protocol in which a 1% propofol formulation, formulated in the same manner as Compound 1, was administered to 5 pigs via a 10-min IV infusion at 0.750 mg/kg/min (7.5 mg/kg total dose).

Data from this study indicated that Compound 1 exhibited a similar pharmacokinetic profile to propofol in the pig model. A three-compartment model best described the Compound 1 and propofol data. Clearance of Compound 1 exceeded estimated hepatic blood flow, similar to propofol. Compound 1 also exhibited a similar metabolic pathway in pigs to that of propofol in humans: glucuronidation in the 1-position with the 4-position being subject to hydroxylation followed by glucuronide and sulfate conjugation. A dose-escalation study in dog showed similar plasma concentrations at washout for Compound 1 and propofol indicating similar clearance rates in that species as well.

Example 9

Anesthetic Effects in Rats

The anesthetic dose response of bolus IV injection of Compound 1, compared to propofol, was studied in rats.

A validated rodent model of general anesthesia (see Hill-Venning C et al., 1996, Neuropharmacology 35, 1209; Lingamaneni R et al., 2001, Anesthesiology 94, 1050) was used to provide a measure of onset and duration of anesthesia as demonstrated by the Loss of Righting Reflex (LORR) and recovery time (time interval from return of righting reflex until the rat was able to grip and climb a steel frame and ambulate normally). Also measured was minimum dose to achieve LORR and maximum tolerated dose (MTD).

A 1% Compound 1 formulation, prepared as described in Example 2 and formulated in accordance with Example 5, or DIPRIVAN was administered by bolus IV injection at 2.5 ml/min to 6 male Sprague-Dawley rats (200-300 g) per dose group for the amount of time required to administer the doses described below. The relative potency was assessed by determining the dose required to cause 50% of the rats to lose righting reflex (HD50) and the dose required to produce 7 minutes of anesthesia (HD7 min). The ranges of doses studied were 2, 3, 4, 7, 14 and 21 mg/kg for Compound 1 and 3.5, 4.0, 7.0 and 14.0 mg/kg for DIPRIVAN.

Results indicated that bolus IV administration of Compound 1 produced dose-dependent duration of anesthesia in rats. Onsets of LORR were less than 15 sec when the respective drugs were administered at a dose of at least 3 mg/kg for Compound 1 and at a dose of at least 7.0 mg/kg for propofol. Compound 1 produced LORR at all doses of at least 3 mg/kg. Propofol produced no LORR in 4 of 6 rats tested at 3.5 mg/kg, but did produce LORR at all other doses tested. Table 1 compares the HD50, HD7 min, MTD, and therapeutic index (TI; defined herein as the ratio of MTD to HD7 min) results for Compound 1 and propofol. One rat died when administered 14 mg/kg DIPRIVAN. Three rats died when administered 21 mg/kg of Compound 1. Recovery time showed little relationship to dose.

TABLE 1

Comparison of HD50, HD7 min, MTD and TI results for Compound 1 and propofol administered by bolus IV to rats.

|  | Propofol | Compound 1 |
| --- | --- | --- |
| HD50 | 3.8 mg/kg | 2.3 mg/kg |
| HD7 min | 7.0 mg/kg | 3.4 mg/kg |

TABLE 1-continued

Comparison of HD50, HD7 min, MTD and TI results for Compound 1 and propofol administered by bolus IV to rats.

|  | Propofol | Compound 1 |
| --- | --- | --- |
| MTD | <14 mg/kg | 14 mg/kg |
| TI | <2 | 4.1 |

In summary, Compound 1 showed potency at lower doses than propofol and also showed a higher MTD and improved TI compared to propofol.

(S)-(+)-2-sec-butyl-6-isopropylphenol, prepared in accordance with Example 2, was also evaluated in this test at doses of 4, 5, 6, 7, 14, 21, 28 and 35 mg/kg. Table 1a indicates HD50, HD7 min, MTD, and TI results for this compound. One of six rats died when administered 28 mg/kg of (S)-(+)-2-sec-butyl-6-isopropylphenol.

TABLE 1a

HD50, HD7 min, MTD and TI results for (S)-(+)-2-sec-butyl-6-isopropylphenol administered by bolus IV to rats.

|  | (S)-(+) |
| --- | --- |
| HD50 | 5 mg/kg |
| HD7 min | 6.7 mg/kg |
| MTD | 21 mg/kg |
| TI | 3.1 |

In summary, the potency of (S)-(+)-2-sec-butyl-6-isopropylphenol was similar to propofol. (S)-(+)-2-sec-butyl-6-isopropylphenol exhibited a higher MTD and improved TI compared to propofol.

Example 10

Anesthetic and Hemodynamic Effects in Beagle Dogs

A dose-escalation study was conducted in dogs to demonstrate the anesthetic and hemodynamic effects of bolus IV administration of Compound 1 compared to propofol.

The endpoints for this study were dose relationship for induction, duration, depth and quality of anesthesia and hemodynamic effects of bolus IV administration of Compound 1 or propofol. A 1% Compound 1 formulation, prepared as described in Example 2 and formulated in accordance with Example 5, and a 1% propofol formulation formulated in the same manner were used.

Electroencephalographic (EEG) measurement of depth of anesthesia was measured with Bispectral Index (BIS), which is one of several systems used to measure the effects of anesthetic drugs on the brain and to track changes in the level of sedation or anesthesia. BIS is a mathematical algorithm that analyzes data from the EEG, and the output is a single number from 100 (fully conscious) to 0 (isoelectric EEG). Other assessments included sedation scores, clinical observations, blood pressure, electrocardiogram (ECG), and oxygen saturation.

Beagle dogs (male, 2-4 years old, 8-10 kg) were implanted with vascular access ports. At the time of implant surgery, the dogs' heads were shaved, marked for EEG electrode placement and injected with BOTOX® (Allergan, Inc., Irvine, Calif.; botulinum toxin type A purified neurotoxin complex): 40 units total per dog in 5 intramuscular (IM) injections across the brow were administered. The injections were intended to suppress muscular movement and electromyographic (EMG) interference with the BIS signal.

The study was a crossover design. Each dog received 2 to 4 escalating bolus IV doses (injected over 60 seconds) of Compound 1 or propofol separated by at least 30 min (or until the dog was awake) until the MTD was achieved. The MTD was defined as the dose that reduced mean arterial blood pressure (MAP) by 50% or to less than 50 millimeters of mercury (mmHg or mm Hg). All animals received supplemental oxygen and, if needed, ventilatory support after 4 min of apnea.

Depth of anesthesia was determined by assessing the presence or absence of lash reflex, response to glabellar tap or auditory stimulus, toe pinch, and breathing. Presence of each sign was scored as 1 and absence of each as 0. This allowed calculation of a Cumulative Sedation Score at multiple time points over the 30 min between doses (5=awake, 0=apneic/deep anesthesia). The quality of anesthesia was assessed by noting the smoothness of induction, qualitative assessment of muscle tone, and presence of involuntary motion. Episodes of involuntary movements (e.g. during emergence) were scored as present or absent throughout the observation period for each dose. BIS and hemodynamic effects were analyzed with 2-way ANOVA followed by t-test with Bonferroni correction for multiple comparisons of the effect of time and dose.

A. Anesthetic Effects

The abilities of Compound 1 and propofol administered by bolus IV to effect dose-related anesthesia in unpremedicated spontaneously breathing beagles (5-30 mg/kg/dose; 3-6 dogs per dose of Compound 1; 1-5 dogs per dose of propofol are demonstrated in Table 2. Two of 3 dogs administered 15 mg/kg of propofol reached the MTD at 15 mg/kg. Therefore, only 1 dog was given the 30 mg/kg propofol dose.

TABLE 2

Dose-related duration of anesthesia (sleep time) for Compound 1 and propofol after bolus IV administration to dogs.

| Dose | Propofol | Compound 1 |
| --- | --- | --- |
| 5 mg/kg | 13 min | 23 min |
| 10 mg/kg | 28 min | 33 min |
| 15 mg/kg | 43 min | 40 min |
| 30 mg/kg | 69 min | 71 min |

The data also indicated that anesthesia was induced within 1 min at all doses for Compound 1 and propofol. Duration of anesthesia, measured by sleep time, was similar at most doses for Compound 1 and propofol. Cumulative sedation scores demonstrated approximately equipotent anesthetic depth for both propofol and Compound 1 above 5 mg/kg. There was no significant difference between BIS values for dogs administered Compound 1 at 10 mg/kg or propofol at 10 mg/kg or 15 mg/kg. Compound 1 produced a greater effect on BIS at doses of at least 15 mg/kg but these doses are very high, and potentially not clinically relevant. The quality of anesthesia (smoothness of induction, qualitative assessment of muscle tone, presence of involuntary motion) of Compound 1 was similar to propofol.

(S)-(+)-2-sec-butyl-6-isopropylphenol, produced in accordance with Example 2, was also evaluated in this test. Table 2a shows the dose-related duration of anesthesia (sleep time) for this compound.

TABLE 2a

Dose-related duration of anesthesia (sleep time) for (S)-(+)-2-sec-butyl-6-isopropylphenol and propofol after bolus IV administration to dogs.

| Dose | (S)-(+) |
| --- | --- |
| 5 mg/kg | 12 min |
| 10 mg/kg | 33 min |
| 15 mg/kg | 50 min |
| 30 mg/kg | 56 min |

The data indicated that duration of anesthesia was similar for Compound 1 and propofol.

B. Hemodynamic Effects: Blood Pressure

Hemodynamic data, such as mean arterial pressure (MAP), were recorded at baseline, 1, 2, 4, 8, 15, 20 and 30 min. Compound 1 was administered at 5, 10, 15 and 30 mg/kg to 6, 4, 3 and 3 dogs respectively. Propofol was administered at the same doses to 3, 5, 5, and 1 dogs, respectively. Only 1 dog received 30 mg/kg propofol because the MTD criteria were reached with 15 mg/kg in two animals. Data were analyzed with a 2-way ANOVA followed by t-test with Bonferroni correction for multiple comparisons.

A comparison of the data indicated that propofol produced a significantly greater effect on MAP than does Compound 1. Table 3 provides an example in which mean arterial pressure percent (MAP %) changes from baseline 4 min after bolus IV administration of 10, 15 or 30 mg/kg of Compound 1 are compared to MAP % changes effected by the same doses of propofol.

TABLE 3

Dose-related mean arterial pressures changes measured as MAP % change from baseline 4 min after bolus IV administration of Compound 1 or propofol.

| Dose | Propofol | Compound 1 |
| --- | --- | --- |
| 10 mg/kg | −22% | 5% |
| 15 mg/kg | −32% | −19% |
| 30 mg/kg | −66%* | −41% |

*Only 1 dog was tested at 30 mg/kg propofol in view of 2 dogs having reached the MTD criteria at 15 mg/kg propofol.

(S)-(+)-2-sec-Butyl-6-isopropylphenol, produced in accordance with Example 2, was also evaluated in this test. A comparison of the data indicated that propofol produced a significantly greater effect on MAP than did (S)-(+)-2-sec-butyl-6-isopropylphenol. Table 3a provides an example, comparing MAP % changes from baseline at 4 min.

TABLE 3a

Dose-related mean arterial pressures changes measured as MAP % change from baseline 4 min after bolus IV administration of (S)-(+)-2-sec-butyl-6-isopropylphenol to dogs.

| Dose | (S)-(+) |
| --- | --- |
| 10 mg/kg | +3% |
| 15 mg/kg | +1% |
| 30 mg/kg | −33% |

Example 11

Anesthetic and Hemodynamic Effects in Pigs

Anesthetic and hemodynamic effects of Compound 1 and propofol were compared in anesthetized ventilated pigs infused IV with a 0.5% Compound 1 formulation, prepared as described in Example 2 and formulated in accordance with Example 6, or DIPRIVAN (1% propofol injectable emulsion). Assessments included EEG measurements of depth of anesthesia using BIS, pharmacokinetics, blood pressure, ECG, heart rate, cardiac output, body temperature, and oxygen saturation.

Experiments were performed on commercial farm-bred swine of either sex (mean weight 33.6 kg). Anesthesia was induced with isoflurane. Intravascular access was obtained from an ear vein. Each pig was intubated and mechanically ventilated. Tissue oxygenation was monitored using continuous pulse oximetry placed on the tongue. Ventilation was monitored using an inspired/expired gas analyzer that measured oxygen, carbon dioxide, and potent inhalation agent concentrations. Ventilator settings were adjusted as needed to maintain steady state.

A continuous level of anesthesia was achieved with isoflurane and an infusion of pancuronium (10 mg/hr). ECG was monitored throughout the study. Arterial blood pressure was monitored through the cannulated left femoral artery. MAP, systolic and diastolic arterial pressures and heart rate were collected every 5 seconds. An internal jugular vein was cannulated with a pulmonary artery catheter for thermodilution estimates of cardiac output and blood temperature. Body temperature was maintained at 37° C. Instrumentation for EEG monitoring was accomplished using an adhesive electrode array over the fronto-occipital regions (Aspect Medical, Norwood, Mass., USA).

The experimental design included a 30 min stabilization period, followed by IV infusion of Compound 1 (0.6 mg/kg/min×20 min) or propofol (0.750 mg/kg/min×10 min). The respective infusion was followed by a 180 min washout period. Hemodynamic measurements and blood samples for pharmacokinetic analysis were taken at pre-infusion, every 2 min during infusion of Compound 1 or propofol and at frequent intervals during the washout period. The infusion times and rates for Compound 1 and propofol were previously determined to produce a maximum reduction of BIS (<10) during the infusion period. Arterial blood samples for determining pH, pO2, pCO2, glucose, potassium, and lactate were measured at baseline before Compound 1 or propofol infusion, during infusion, and hourly after infusion.

A. Anesthetic Effects

Compound 1 and propofol produced maximal suppression of BIS (<10) with IV infusions of 17.3±1.9 min of 0.6 mg Compound 1 per kg per min and 9.4±1.9 min of 0.750 mg propofol per kg per min, respectively. The effect on EEG was reversible and returned to baseline within 60 min.

B. Hemodynamic Effects

Figure 3:
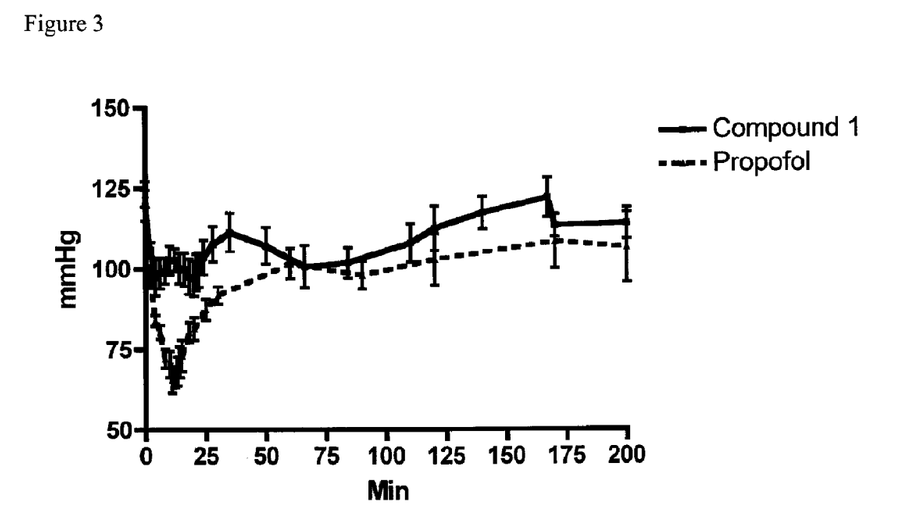
FIG. 3 shows the effect on mean arterial blood pressure (mm Hg) in pigs following IV infusion of the (−) stereoisomer of formula (I) in which X is H in comparison with propofol.
Figure 4:
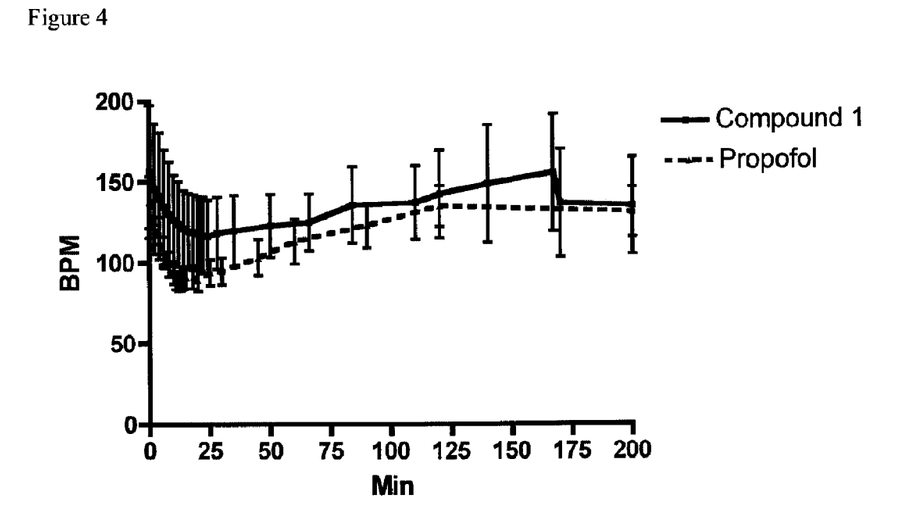
FIG. 4 shows the effect on heart rate (beats per minute) in pigs following IV infusion of the (−) stereoisomer of formula (I) in which X is H in comparison with propofol.

Mean arterial pressure and heart rate were measured at intervals throughout IV infusion and washout with Compound 1 (0.6 mg/kg/min, 6 pigs) and propofol (0.750 mg/kg/min, 6 pigs). Results are shown in FIGS. 3 and 4 respectively. Arterial blood gas samples from pigs infused with Compound 1 were taken and analyzed for blood gas and serum chemistry values.

Baseline MAP and HR values were not different between Compound 1 and propofol. Both compounds reduced MAP, but propofol produced a significantly larger decrease in MAP than Compound 1. The lowest HR measured for propofol was significantly lower than the lowest HR measured for Compound 1. Both HR and MAP returned to baseline after discontinuation of infusions of Compound 1 or propofol.

Arterial blood gas and serum chemistry values were within normal limits. Compound 1 did not produce any significant metabolic alterations such as metabolic acidosis or increased lactate.

Example 12

Anti-emetic Activity

Compound 1 was tested for its anti-emetic potential in ferrets and compared to that of propofol.

Male descented ferrets weighing 1.0-1.5 kg with vascular access ports in the jugular vein were housed on a 12/12-hour light/dark cycle under controlled temperature, with food and water provided ad libitum. On each study day, food was presented to ferrets one hour prior to dosing. Immediately prior to dosing, food and water were removed. A 1% Compound 1 formulation, prepared as described in Example 2 and formulated in accordance with Example 5, or DIPRIVAN was administered by IV infusion to the ferrets; see Wynn R L et al, 1993, Eur J Pharmacol 241, 42 re DIPRIVAN administration in ferrets. After administration of Compound 1 or DIPRIVAN, animals were placed in clean, transparent cages (with lids) and left unrestrained for a 45-min observation period by an observer blinded to the specific treatment administered.

Emesis in ferrets is characterized by rhythmic abdominal contractions that are associated either with the oral expulsion of solid or liquid material from the gastrointestinal tract (i.e., vomiting) or with movements that do not include passage of material (i.e., retching). Episodes of retching and/or vomiting were considered separate episodes when the interval between retches and/or vomits exceeded 5 sec.

Pro-emetic activity of Compound 1 or propofol was studied in 6 ferrets per drug as follows: Ferrets were anesthetized by isoflurane inhalation. Compound 1 or propofol was administered by an IV infusion for 15 min at 1 mg/kg/min. After termination of the infusion, the ferrets were observed continuously for 45 min, and the number of vomits and retches were counted.

Anti-emetic activity of Compound 1 or propofol was studied in 6 ferrets per drug as follows: Ferrets were anesthetized with isoflurane, administered Compound 1 or propofol by a 15 min IV infusion at 1 mg/kg/min. After termination of the infusion, 0.5 mg/kg morphine sulfate was administered subcutaneously and the ferrets were monitored for 45 min as described above. Six additional ferrets were administered subcutaneously 0.5 mg/kg morphine sulfate only.

Morphine sulfate (0.5 mg/kg) alone was pro-emetic in ferrets, yielding 15 episodes of vomiting and 157 retches. Compound 1 did not produce any episodes of vomiting or retching when administered alone. Ferrets administered Compound 1 in the presence of morphine exhibited 1 vomit and 47 retches. Ferrets that received propofol and morphine sulfate exhibited 3 vomits and 47 retches. Therefore, Compound 1 and propofol both reduced the incidence of vomiting and retching in the presence of morphine.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A (+)-stereoisomer of formula (I):

wherein X is H or F; or a salt or prodrug thereof.

2. The compound of claim 1, wherein X is H.

3. The compound of claim 1, which is a (+)-stereoisomer of formula (I) or a pharmaceutically acceptable salt or prodrug thereof.

4. The compound of claim 3, wherein X is H.

5. A pharmaceutical composition comprising the compound of claim 3, and a pharmaceutically acceptable carrier.

6. The pharmaceutical composition of claim 5, wherein X is H.

7. The pharmaceutical composition of claim 5, which is formulated for intravenous administration.

8. The pharmaceutical composition of claim 7, wherein X is H.

9. The pharmaceutical composition of claim 7, which is formulated as a lipid emulsion.

10. The pharmaceutical composition of claim 9, wherein X is H.

11. The compound of claim 3, which is a (+)-stereoisomer of formula (I) or a pharmaceutically acceptable salt thereof.

12. The compound of claim 11, wherein X is H.

13. A pharmaceutical composition comprising a compound of formula (I):

wherein the compound is a (+)-stereoisomer of formula (I) and wherein X is H or F; or a pharmaceutically acceptable salt thereof and a pharmaceutically acceptable carrier.

14. The pharmaceutical composition of claim 13, wherein X is H.

15. The pharmaceutical composition of claim 13, which is formulated for intravenous administration.

16. The pharmaceutical composition of claim 15, wherein X is H.

17. The pharmaceutical composition of claim 15, which is formulated as a lipid emulsion.

18. The pharmaceutical composition of claim 17, wherein X is H.

19. A method for inducing or maintaining general anesthesia in an animal comprising administering to the animal an effective amount of a (+)-stereoisomer of formula (I):

wherein X is H or F; or a pharmaceutically acceptable salt or prodrug thereof.

20. The method of claim 19, wherein X is H.

21. The method of claim 19, wherein the compound is a (+)-stereoisomer of formula (I) or a pharmaceutically acceptable salt thereof.

22. The method of claim 19, comprising administering to the animal an effective amount of a (+)-stereoisomer of formula (I) in which X is H, or a pharmaceutically acceptable salt thereof.

23. A method for inducing or maintaining general anesthesia in an animal comprising administering to the animal an effective amount of the pharmaceutical composition of claim 15.

24. The method of claim 23, wherein X is H.

25. A method for promoting sedation in an animal comprising administering to the animal an effective amount of a (+)-stereoisomer of formula (I):

wherein X is H or F; or a pharmaceutically acceptable salt or prodrug thereof.

26. The method of claim 25, wherein X is H.

27. The method of claim 25, wherein the compound is a (+)-stereoisomer of formula (I) or a pharmaceutically acceptable salt thereof.

28. The method of claim 25, comprising administering to the animal an effective amount of a (+)-stereoisomer of formula (I) in which X is H, or a pharmaceutically acceptable salt thereof.

29. A method for promoting sedation in an animal comprising administering to the animal an effective amount of the pharmaceutical composition of claim 15.

30. The method of claim 29, wherein X is H.

31. A process for preparing a (+)-stereoisomer of formula (I)

wherein X is H or F; or a salt or prodrug thereof, which comprises
(a) hydrolysing a carbamic acid (+)-2-sec-butyl-6-isopropylphenyl ester diastereomer of formula:

in which R¹ represents a chiral amino group;
(b) diazotizing a corresponding (+)-2-sec-butyl-6-isopropyl aniline of formula or
(c) reducing a corresponding 2-(1-methylallyl)-6-isopropylphenol of formula followed if required by forming the free phenol or salt or pro-drug thereof.

32. The process of claim 31, wherein the salt is a pharmaceutically acceptable salt.

33. The process of claim 31, wherein X is H.

34. The process of claim 31, wherein the method comprises forming the free phenol or salt or pro-drug thereof.

35. The process of claim 34, wherein X is H.

36. The process of claim 34, wherein the method comprises forming the free phenol or pharmaceutically acceptable salt or pro-drug thereof.

37. The process of claim 36, wherein X is H.

38. The process of claim 36, wherein the method comprises forming the free phenol or pharmaceutically acceptable salt.

39. The process of claim 38, wherein X is H.

40. A carbamic acid (+)-2-sec-butyl-6-isopropylphenyl ester diastereoisomer of formula in which R¹ represents a chiral amino group, and in which X is H or F.

41. A diastereoisomer of claim 40, wherein R¹ represents an (S)-1-arylethylamino group.

* * * * *